(12) United States Patent
Ponomarenko et al.

(10) Patent No.: US 8,235,957 B2
(45) Date of Patent: Aug. 7, 2012

(54) ABSORBENT ARTICLE WITH SUBLAYER

(75) Inventors: Ekatarina Anatolyevna Ponomarenko, Bad Soden (DE); Monika Imgard Johanning, Steinbach/Ts (DE); Ralf Geilich, Eppstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/525,614

(22) Filed: Sep. 22, 2006

(65) Prior Publication Data
US 2007/0073256 A1 Mar. 29, 2007

(30) Foreign Application Priority Data

Sep. 23, 2005 (EP) .................................... 05108795

(51) Int. Cl.
*A61F 13/15* (2006.01)
*A61F 13/20* (2006.01)
(52) U.S. Cl. .................................. 604/385.01; 604/378
(58) Field of Classification Search .................. 604/378, 604/381–383, 385.101
See application file for complete search history.

(56) References Cited

U.S. PATENT DOCUMENTS

| | | | |
|---|---|---|---|
| 3,860,003 A | 1/1975 | Buell | |
| 4,276,338 A * | 6/1981 | Ludwa et al. | 428/137 |
| 4,610,678 A | 9/1986 | Weisman et al. | |
| 4,834,735 A | 5/1989 | Alemany et al. | |
| 4,895,749 A * | 1/1990 | Rose | 428/132 |
| 4,940,464 A | 7/1990 | Van Gompel et al. | |
| 5,092,861 A | 3/1992 | Nomura et al. | |
| 5,151,092 A | 9/1992 | Buell et al. | |
| 5,246,433 A | 9/1993 | Hasse et al. | |
| 5,260,345 A | 11/1993 | DesMarais et al. | |
| 5,300,054 A * | 4/1994 | Feist et al. | 604/378 |
| 5,342,338 A | 8/1994 | Roe | |
| 5,368,909 A * | 11/1994 | Langdon et al. | 428/137 |
| 5,387,207 A | 2/1995 | Dyer et al. | |
| 5,397,316 A | 3/1995 | LaVon et al. | |
| 5,478,335 A * | 12/1995 | Colbert | 604/383 |
| 5,509,914 A | 4/1996 | Osborn | |
| 5,533,991 A | 7/1996 | Kirby et al. | |

(Continued)

FOREIGN PATENT DOCUMENTS

EP 0 203 823 A2 12/1986

(Continued)

OTHER PUBLICATIONS

International Search Report.

*Primary Examiner* — Michele M Kidwell
(74) *Attorney, Agent, or Firm* — Kathleen Y. Carter; John G. Powell

(57) ABSTRACT

An absorbent article includes a backsheet and a sublayer. The sublayer including at least a first acquisition layer and a second acquisition layer. The sublayer includes one or more areas with a plurality of combined holes. The combined holes are formed by holes extending through the first acquisition layer and holes in or extending through the second acquisition layer, or by holes in or extending through the second acquisition layer and indentations in the first acquisition layer. The combined holes have an average smallest dimension of at least 2 mm, and the surface areas of the holes through the first layer, or of the indentations in the first layer, are less than the corresponding surface areas of the holes in or through the second layer.

7 Claims, 4 Drawing Sheets

U.S. PATENT DOCUMENTS

| | | |
|---|---|---|
| 5,554,145 A | 9/1996 | Roe et al. |
| 5,569,234 A | 10/1996 | Buell et al. |
| 5,603,707 A | 2/1997 | Trombetta et al. |
| 5,625,222 A | 4/1997 | Yoneda et al. |
| 5,628,097 A | 5/1997 | Benson et al. |
| 5,658,639 A | 8/1997 | Curro et al. |
| 5,718,928 A * | 2/1998 | Rieker .......................... 425/290 |
| 5,885,267 A | 3/1999 | Mishima et al. |
| 5,897,543 A * | 4/1999 | Francis ........................ 604/383 |
| 5,897,545 A | 4/1999 | Kline et al. |
| 5,916,661 A | 6/1999 | Benson et al. |
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,398,679 B1 * | 6/2002 | Brown ............................ 474/35 |
| 6,423,884 B1 | 7/2002 | Oehmen |
| 6,458,111 B1 | 10/2002 | Onishi et al. |
| 6,528,698 B2 | 3/2003 | Mizutani et al. |
| 6,590,138 B2 * | 7/2003 | Onishi .......................... 604/378 |
| 6,600,085 B2 * | 7/2003 | Sun et al. ...................... 602/56 |
| 6,786,894 B2 | 9/2004 | Divo et al. |
| 6,897,350 B2 | 5/2005 | Yagou et al. |
| 7,005,558 B1 * | 2/2006 | Johansson et al. ............ 604/383 |
| 7,067,711 B2 | 6/2006 | Kuroda et al. |
| 7,132,585 B2 * | 11/2006 | Kudo et al. ................... 604/380 |
| 2003/0045851 A1 | 3/2003 | Vartiainen |
| 2003/0093048 A1 | 5/2003 | McBride |
| 2003/0139719 A1 | 7/2003 | Nanaumi et al. |
| 2003/0187417 A1 | 10/2003 | Kudo et al. |
| 2003/0233082 A1 | 12/2003 | Kline et al. |
| 2004/0087927 A1 * | 5/2004 | Suzuki ......................... 604/378 |
| 2004/0167486 A1 | 8/2004 | Busam et al. |
| 2005/0234410 A1 | 10/2005 | Ashton et al. |
| 2005/0256475 A1 | 11/2005 | Komatsu et al. |
| 2006/0122569 A1 * | 6/2006 | Drevik et al. ................. 604/360 |

FOREIGN PATENT DOCUMENTS

| | | |
|---|---|---|
| EP | 0 953 324 A1 | 11/1999 |
| EP | 1 201 212 A2 | 5/2002 |
| WO | WO 90/14813 A1 | 12/1990 |

* cited by examiner

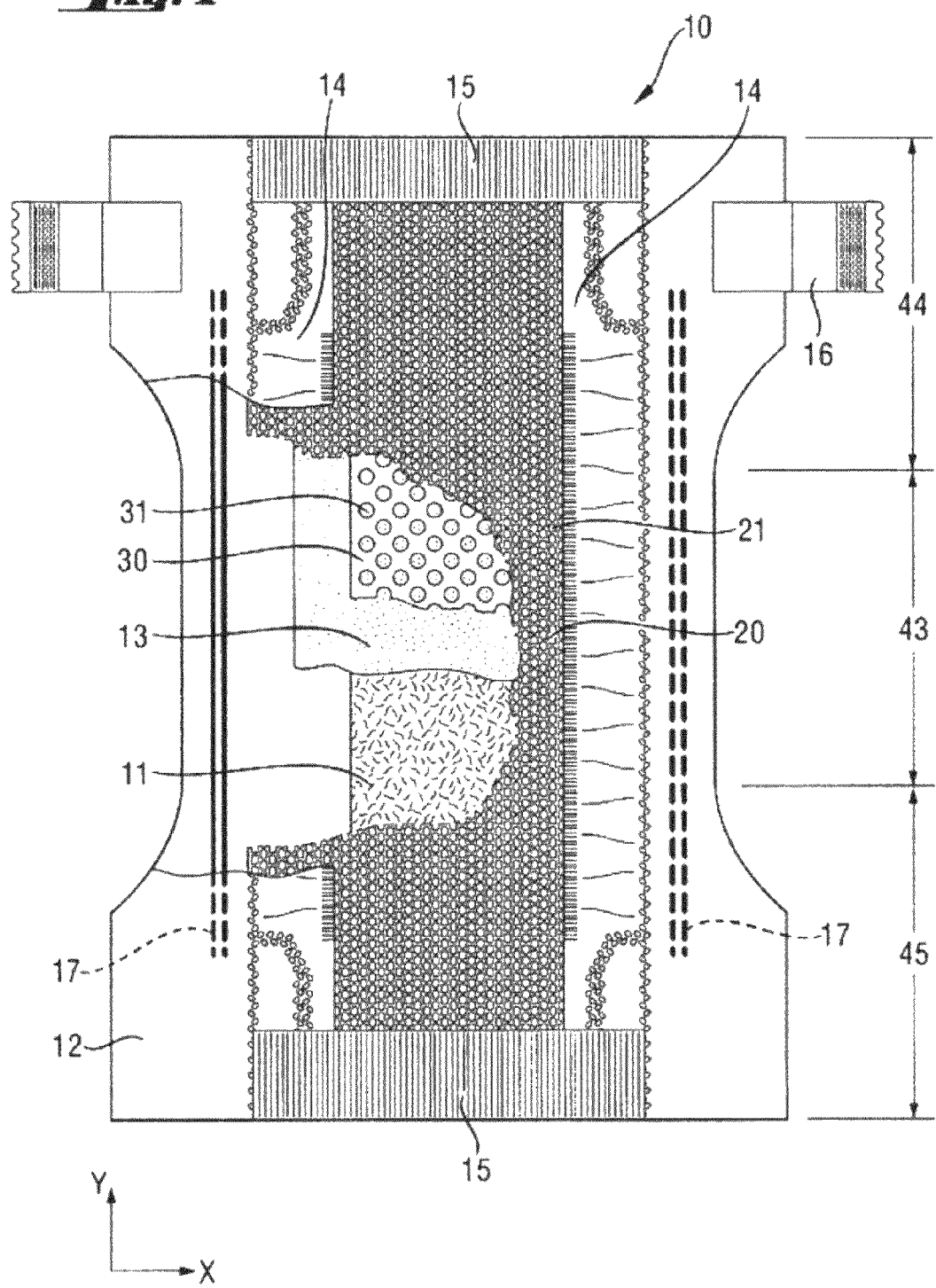

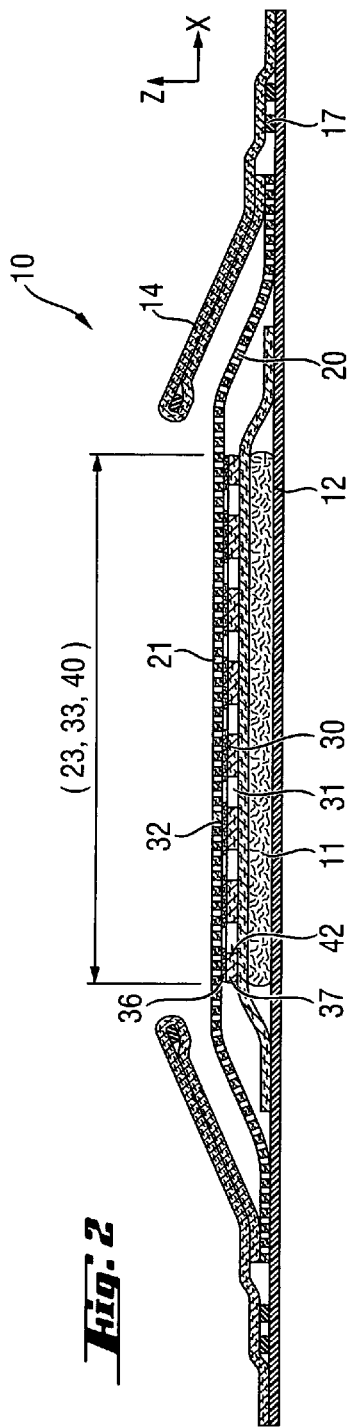
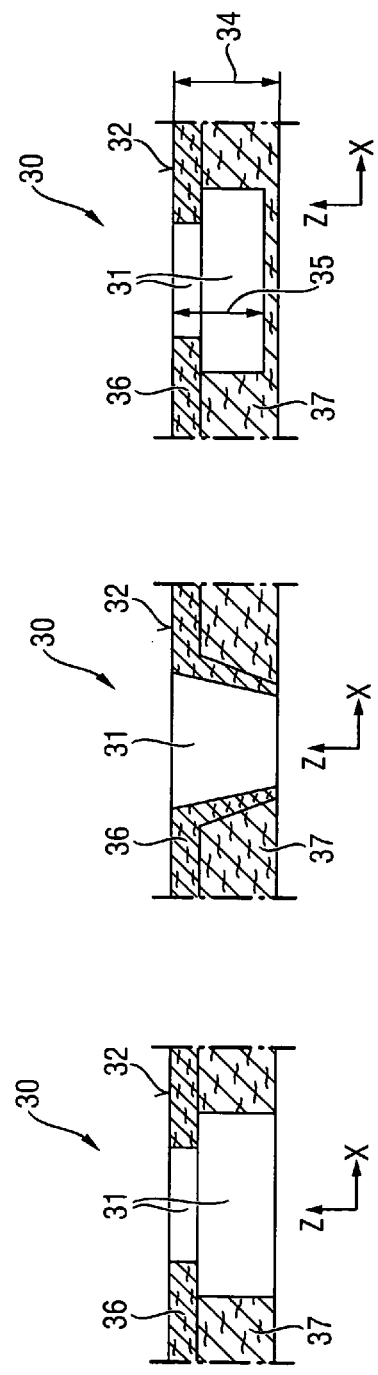

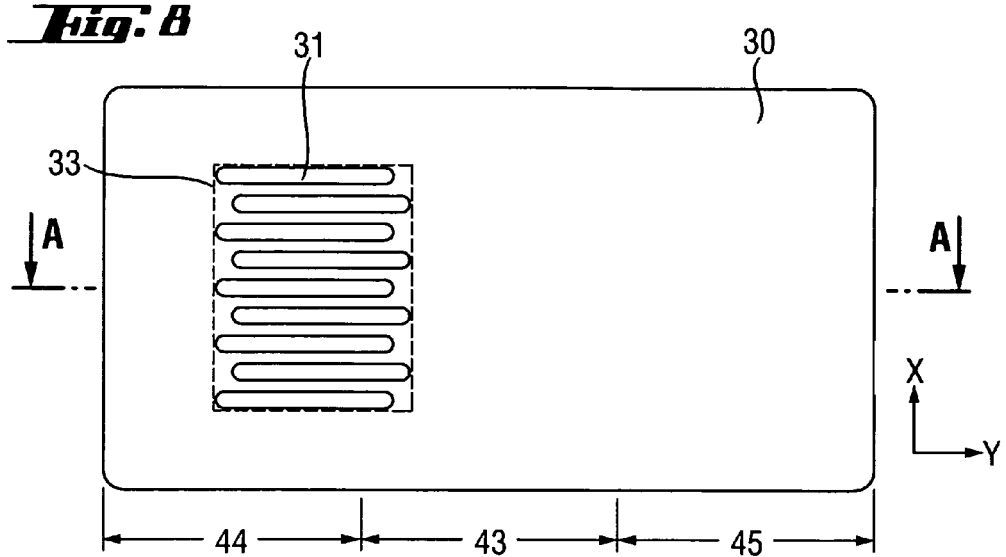
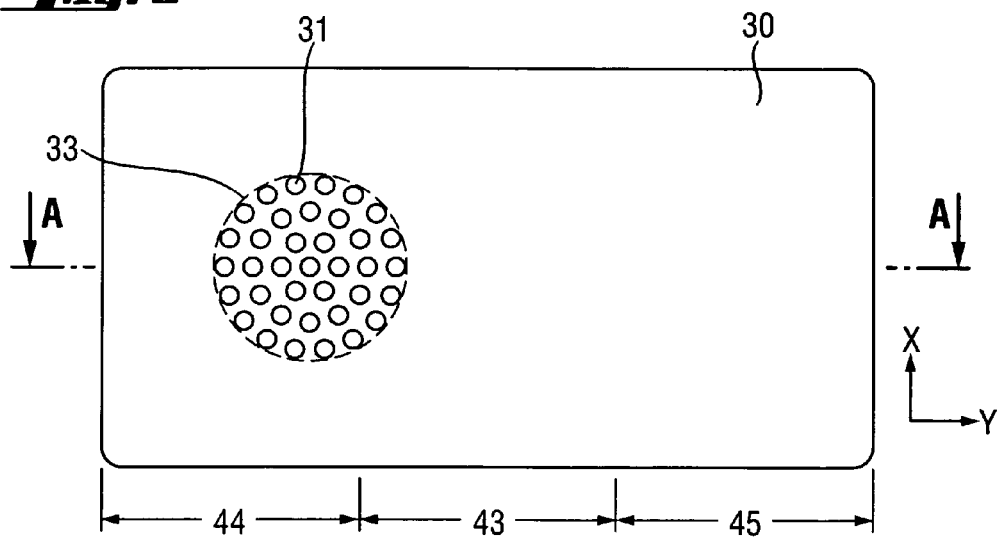
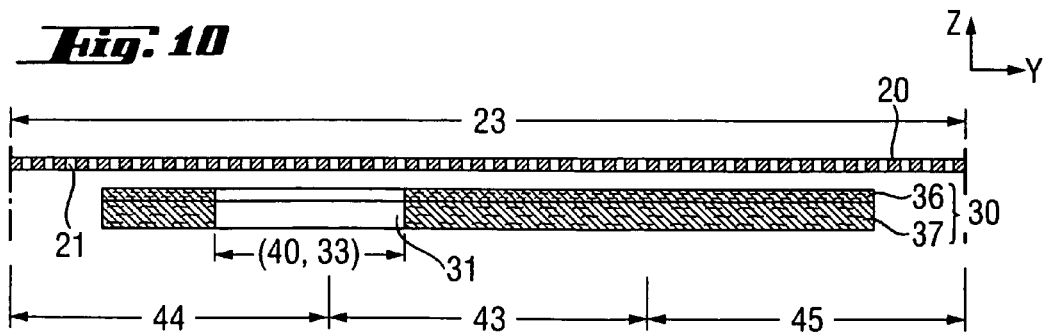

ABSORBENT ARTICLE WITH SUBLAYER

FIELD OF THE INVENTION

This invention is directed to an absorbent article, preferably a diaper or training pants, having a backsheet, absorbent core and topsheet and a sublayer (30) formed from at least a first and second acquisition layer (36, 37) with a multitude of z-direction holes (31) that are formed by holes in or through both said layers, which provides a very efficient isolation of feces away from the skin and at the same time liquid acquisition.

BACKGROUND OF THE INVENTION

It is well known that fecal material is often difficult to remove from the skin of the user, in particular on sensitive skin such as by young babies and the skin around the genitals. Moreover, it is well known that fecal material on the skin can cause irritation and redness of the skin and some times even dermatitis of the skin.

One of the solutions to reduce the fecal material on the skin is to provide a means to isolate the fecal material immediately after discharge, away from the skin. The problem with feces isolation in diapers is that the feces can vary hugely in consistency and viscosity and furthermore that, whilst isolating the feces, the diaper needs to retain its urine absorption capacity.

Hereto, diapers have been suggested with a topsheet with one or more large openings, through which the feces can pass to a void space between the topsheet and the absorbent core. The fecal material is then stored underneath this topsheet, away from the skin.

As alternative, a diaper with a first topsheet with a multitude of small openings has been proposed, allowing low viscosity feces to pass through said openings onto the absorbent core, such that it may be isolated underneath said topsheet and such that the absorbent core may dewater the feces, such as for example described in U.S. Pat. No. 5,342,338. Optionally, a second topsheet with openings may be present, which further allows immobilization of the feces and dewatering of the feces by the absorbent core underneath.

Also various other feces management element that comprise high loft or loop materials have been proposed.

Disclosed herein is an improved way to provide i) feces isolation and immobilization, ii) reduced re-soiling of the skin by the immobilized feces and iii) good liquid acquisition at the same time. This is achieved by providing an absorbent article, e.g. diaper, comprising a sublayer that includes at least two acquisition layers and combined holes or indentations in or through both of the acquisition layers. The sublayer, by way of the combined holes, being capable of receiving, storing and immobilizing feces, and simultaneously acquiring liquid (e.g., urine).

Furthermore, it is beneficial that the holes or indentations in the first acquisition layer are smaller in cross-section surface area (in the plane of the sublayer) than the holes in or through the second layer, to provide improved feces entrapment and/or to provide a reduced risk that the material of the second acquisition layer (e.g. unbonded or partially bonded fibers) or the material of the absorbent core underneath may come in contact with the skin of the user. Thus, a more comfortable diaper with a sublayer is obtained that provides a better feces immobilization whilst still allowing excellent liquid acquisition.

BRIEF DESCRIPTION OF THE DRAWINGS

FIG. 1 is a plan top view of a diaper (10) of the invention, with cut out portions to show the sublayer (30) as described herein.

FIG. 2 shows a cross-section view of the diaper (10) of FIG. 1 through the x-direction centre line thereof.

FIG. 3 shows a cross section through a hole (31) and surrounding parts of a sublayer (30) of the diaper (10) of the invention as also shown in FIGS. 1 and 2.

FIG. 4 shows a cross section through a hole (31) and surrounding parts of another preferred sublayer (30) herein.

FIG. 5 shows a cross section through a hole (31) and surrounding parts of another sublayer (30) herein.

FIG. 8 shows a plan top view of a possible sublayer (30) for use herein having a rectangular region (33) with rectangular holes with in the surface in the back region (44) and partial crotch region (43) of the diaper (10).

FIG. 9 shows a plan top view of preferred sublayer (30) for use herein having a circular region (33) with holes with a circular circumference in the back region (44) and partial crotch region (43) of the diaper (10).

FIG. 10 shows a cross section view of the sublayer (30) of FIG. 8 and a topsheet (20), taken along the y-direction centre line thereof, forming an overlap region (40).

DETAILED DESCRIPTION OF THE INVENTION

Figure 7:
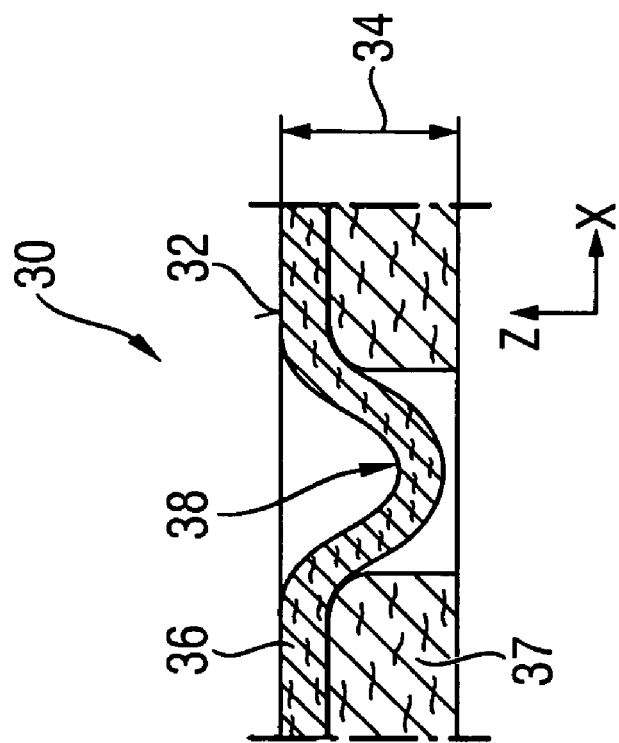
FIG. 7 shows a cross section through a hole (31) and surrounding parts of yet another preferred sublayer (30) herein.

Whilst the invention has been derived while investigating improved feces isolation and immobilization, the sublayer (30) as described herein may also be used in articles other than those intended for feces handling, for example in sanitary napkins or even panty-liners When used herein, "diaper" means any article intended for use by a baby or infant for collection of feces and/or urine, including, amongst others, also training pants. "Adult incontinence garment", when used herein, includes any article intended for adults for collection of feces and/or urine.

The article (10) and components thereof, e.g. the backsheet (11), topsheet (20) and sublayer (30) herein, have a length in longitudinal or y-direction (or Machine Direction), a width in transverse or x-direction (or Cross Machine Direction) and a thickness or caliper in z-direction, as shown in the Figures.

The article (10) and optionally components thereof has a back region (44), crotch region (43) and front region (45), that in use are positioned towards the back, in the crotch, or towards the front of the user, respectively. They typically represent herein each ⅓ of the length of the article.

The surface area of the aperture (21) and combined hole (31), as referred to herein, and as used herein to obtain the open area values herein, is the surface area of the cross-section of the aperture (21) or combined hole (31) in the plane of the body-facing surface of the topsheet (20) and the body-facing surface (32) of the sublayer (30), respectively. The average minimum and maximum dimensions of the apertures and holes (31) as used herein is also determined in the cross-section of the aperture (21) or hole (31) in the plane of the body-facing surface of the topsheet (20) and of the sublayer (30).

FIG. 1 is a plan view of a preferred diaper (10) according to the present invention. The diaper is shown in its flat out, uncontracted state (i.e., without elastic induced contraction). Portions of the structure are cut away to more clearly show the underlying structure of the diaper (10). The portion of the diaper (10) that contacts a wearer is facing the viewer.

The diaper (10) comprises a topsheet (20), as described hereinafter in detail, a backsheet (12), and typically an absorbent core (11), and optionally a core wrapping material (13), and a sublayer (30), as described herein after in detail. Further optional features may be present, such elasticized leg cuffs or elastics (17), barrier cuffs (14), elastic waist feature(s) (15). One end portion of the diaper (10) is configured as a first or front (waist) region (45) of the diaper (10). The opposite end portion is configured as a second, back (waist) region (44) of the diaper (10). An intermediate portion of the diaper (10) is configured as a crotch region (43), which extends longitudinally between the first and second waist regions (44, 45). The crotch region (43) is that portion of the diaper (10) which, when the diaper (10) is worn, is generally positioned between the wearer's legs. The diaper (10) is depicted with its longitudinal axis (Y) and its transverse axis (X). The diaper may also comprise a fastening system, which may include at least one fastening member (16) and at least one landing zone (not shown). Preferred diaper configurations are described generally in U.S. Pat. Nos. 4,940,464, 5,554,145; 5,569,234; 6,004,306, U.S. patent application Ser. No. 10/171,249 and in U.S. patent application Ser. No. 10/824,121.

The absorbent core (11) in FIG. 1 is disposed between the sublayer (30) and the backsheet (12). The absorbent core (11) may comprise any absorbent material that is generally compressible, conformable, non-irritating to the wearer's skin, and capable of absorbing and retaining liquids such as urine. Exemplary absorbent core structures (11) for use as the absorbent articles (10) herein are for example described in U.S. Pat. Nos. 4,610,678; 4,834,735; 5,260,345; 5,387,207; 5,397,316; and 5,625,222. Preferably, the absorbent core (11) comprises at least a super absorbent material, preferably a superabsorbent polymer material, also referred to as SAP or AGM, that is capable of absorbing at least about 5 times, preferably at least 10 times, its weight of an aqueous fluid such as 0.9% saline as measured using the Centrifuge Retention Capacity test, well known in the art.

The absorbent material in the absorbent core (11) may have a "profiled" distribution, whereby the absorbent core comprises more absorbent material in one area (e.g. the p-point or crotch and optionally front region) than in another area (e.g. back region).

The absorbent core (11) may also comprise a structuring agent or matrix agent, such as absorbent fibrous material, such as airfelt fibers, and/or adhesive, which each may serve to immobilize the water-swellable material.

However, it may be preferred that a relatively low amount or no absorbent fibrous (cellulose) material is used in the absorbent core (11). Thus, it may be preferred that said core (11) herein comprises large amounts of the water-swellable material and only very little or no absorbent (cellulose) fibers, preferably less than 20% by weight of the water-swellable material, or even less than 10% by weight of the water-swellable material, or even less than 5% by weight.

Preferred absorbent cores (11) herein comprise an adhesive or thermoplastic material or preferably a (fibrous) thermoplastic adhesive material, which is laid down onto a layer of water-absorbing and/or -swellable material. Thereby, the thermoplastic or adhesive material provides cavities to hold the water-swellable material and thereby immobilizes this material. Also, the thermoplastic or adhesive material bonds to the substrate and thus affixes the water-swellable material to the substrate. It may be preferred that no absorbent fibrous material is present in the absorbent core (11).

A particularly preferred absorbent core (11) for liquid (e.g. urine) storage is described in U.S. patent application Ser. No. 10/776,839.

The backsheet (12) is preferably joined to the topsheet (20), and optionally the sublayer (30) at least about a portion of the periphery thereof. The backsheet (12) is preferably manufactured from at least a (thin) polymer film. In one preferred embodiment the film comprising backsheet (12) is impervious to liquids. Typically, the backsheet (12) comprises a layer of polyethylene film having a basis weight between about 10 $g/m^2$ and about 30 $g/m^2$, although other flexible, liquid impervious materials can be used. Preferably, the film is breathable (e.g. via micropores) so as to permit vapors to escape from the diaper (10) while still preventing exudates from passing through the backsheet (12). Particularly preferred backsheet materials have a nonwoven laminated to the film layer so as to make backsheet (12) more "cloth-like". Such a nonwoven layer may comprise a nonwoven material (e.g. one having a spunbonded or other suitable structure) with a basis weight between about 15 $g/m^2$ and about 25 $g/m^2$. Suitable materials for use as backsheet (12) are available form Clopay Plastic Products Company of Mason, Ohio.

The diaper (10) may also include such other features (not shown) as are known in the art including front and rear ear panels, waist cap features, elastics, topsheet (20)s with aperture(s) and elastics, and the like to provide better fit, containment and aesthetic characteristics. Such additional features are well known in the art and are e.g., described in U.S. Pat. No. 3,860,003 and U.S. Pat. No. 5,151,092 and EP1201212-A.

The preferred absorbent articles herein are refastenable diapers (10) (diapers with fasteners) and pant-type diapers, i.e. training pants. Suitable pant-type diapers are disclosed in U.S. Pat. Nos. 5,246,433; 5,569,234; 6,120,487; 6,120,489; 4,940,464; 5,092,861; 5,897,545; 5,957,908 and in Published US Pat. Application 2003/0233082A1.

Sublayer (30)

The sublayer (30) herein serves as an acquisition layer and optionally also as a distribution layer, capable to at least acquire liquid (urine) and temporarily hold the liquid and to allow it to pass, or optionally to transport it, to the absorbent core underneath (in Z-direction), and optionally to also distribute it in the X- and Y-direction of the sublayer (30). It typically does not serve to hold or store fluid (urine) for a longer period or permanently, but it facilitates the absorption of the fluid by the absorbent core below. However, the sublayer of the article (10) of the invention does also serve to store and/or immobilize fecal material in the combined holes (31) of the sublayer (30).

The sublayer (30) herein comprises two acquisition layers or more and the combined holes (31) are formed by indentations or holes to the first acquisition layer (36) (facing the wearer in use) and holes in or through (or when more then two layers are present: optionally indentations in) the second (37) and further acquisition layers. Thus, each hole or indentation in the first acquisition layer (36) has a corresponding hole in or through the second acquisition layer (37) (or optionally: indentation in the second acquisition layer (37)), to thus form a combined hole (31).

The sublayer (30) herein comprises typically two or more hydrophilic acquisition layers (36, 37) and it typically does not comprise any super-absorbent materials, or water-swelling materials, such as generally referred to as SAP and AGM particles, further described herein above.

The second acquisition layer (37) comprises fibers that are typically unbonded or partially bonded. Preferably, the first acquisition layer (36) comprises also fibers, which are however bonded, e.g. preferred are carded bonded nonwoven fibrous webs, as described below.

Figure 6:
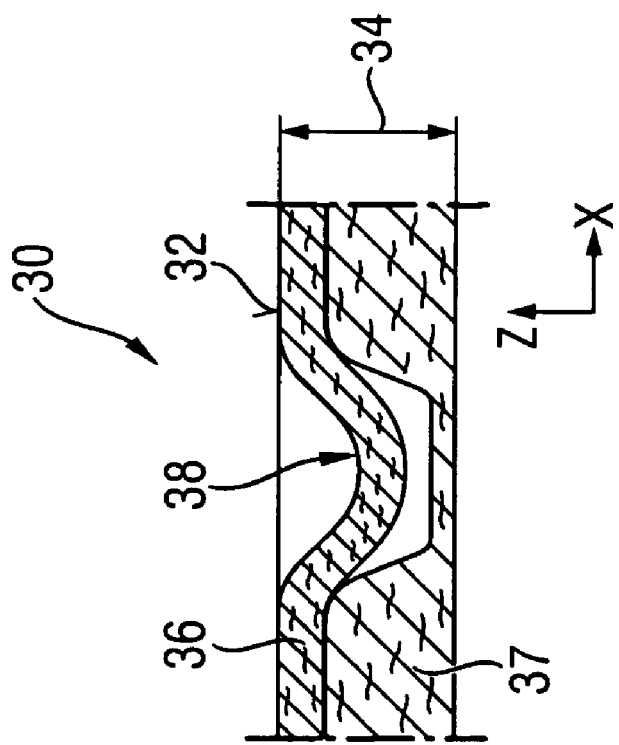
FIG. 6 shows a cross section through a hole (31) and surrounding parts of yet another preferred sublayer (31) herein.

The combined holes (31) of the sublayer (30) herein are capable to store and immobilize feces and they include blind combined holes, as for example shown in FIGS. 5, 6 and 7, and through combined holes, as for example shown in FIGS. 1, 2, 3 and 4. When the holes (31) are blind holes (38), it is still preferred that the holes (31) have an average depth or caliper that is about 50% to 95% of the average thickness or caliper of (relevant region of) the sublayer (30).

The holes (31) of the sublayer (30), as measured on the wearer-facing surface of the sublayer, have an average smallest dimension of 2 to 10 mm, preferably from 3 mm to 10 mm, or more preferably from 4 mm to 8 mm, or even more preferably from 5 mm to 7 mm, said average being the average over the total of smallest dimensions of the holes (31) in the sublayer (30). This can be determined by the method described herein below.

The circumference of the holes (31) of the sublayer (30) may have any form, including rectangular (so that the holes (31) are in the form of stripes or channels), as shown in FIG. 8, but preferably the holes (31) are square, oval, or more preferably the sublayer (30) comprises holes (31) with a circular circumference, including thus preferably substantially cylindrical holes (31), as shown in FIGS. 1 and 9.

Preferably, a hole is such that the smallest dimension is through the centre point of said hole.

The average shortest (smallest) distance between neighboring holes (31) (from edge to edge, in the plane of the surface facing the wearer) is preferably from 2 mm to 10 mm, or more preferably from 3 mm to 7 mm.

The surface areas of the x-y cross section of the holes through the first layer (36), or of the indentations in the first layer (36), are less than the corresponding surface areas of the x-y cross section of the holes in or through the second layer (37), measured on the surface of the second layer (37) that faces the first layer (36).

(Hereby, the x-y cross section of each hole in the first layer (36) is taken at the surface of the sublayer (30) that faces the wearer in use, and the x-y cross section of each hole in the second layer (37) is taken at the surface of that layer that faces the first layer (36), and so forth for subsequent layers).

In one embodiment (and in particular when the first acquisition layer (36) is not present on the z-direction extending walls of the holes of the second layer (37), as described below), it may be preferred that the surfaces areas of all x-y cross sections of a hole or indentation of the first layer (36) are smaller thane the surface areas of all x-y cross sections of a corresponding hole (or indentation) of the second layer (37), as shown in FIGS. 3-7.

For clarity, the x-y dimensions given for the combined holes (31) herein equal the x-y dimensions of the holes or indentations of the first acquisition layer (36), because the combined hole (31) dimensions are taken on the surface of the sublayer (30) that faces the wearer in use. Furthermore, it should be understood that not all of the combined holes (31) necessarily have the same x-y dimensions as the holes or indentations of the first acquisition layer (36). Typically, at least 50% of the combined holes, preferably at least 90%, or even more preferably at least 95% or even 100% of the combined holes (31) have the same x-y dimensions as the holes or indentation of the first acquisition layer (36).

Highly preferred is that the (material of) the first acquisition layer (36) is not only present on the surface of the x-y direction extending wearer-facing surface of the second layer, but that it is also present on the substantially z-direction extending walls of the holes or indentations of the second acquisition layer (37), as shown in FIGS. 4, 6 and 7. This helps to reduce or avoid contact of unbonded or partially bonded fibers from the second acquisition layer (37) with the skin of the user.

It may also be optional that the (material of the) first acquisition layer (36) is also present on the bottom wall of the hole through the second acquisition layer (37); as also shown in FIGS. 6 and 7, this may typically be achieved by providing indentations in the first layer (36), rather than holes.

When further acquisition layers are present, they may be present either underneath the second layer (37) (thus between the second layer and the backsheet) or underneath the first layer (36), and thus between the first layer (36) and second layer (37), or both. Such a further acquisition layer may have the same properties as the first or second layer. However, if a further acquisition layer comprises unbonded or partially bonded fibers, like the second layer (37), it would have holes with a circumference and x-y cross sectional surface areas, that are smaller than the corresponding circumference or x-y cross sectional surface of the first layer, as described above.

The sublayer (30) may also comprise additional components, e.g. layers that do not serve as acquisition layers, provided these components to not impede the formation or existence of the combined holes (31) described herein.

Preferred may be that the sublayer (30) has one or more regions (33) with combined holes (31) and regions without combined holes (31). Preferred may be that the sublayer (30) herein has one or more regions (33) with through holes or blind holes (38) that has an open area of from 15% to 50% of the total surface are area of said region (33), (whereby the open area is the sum of the surface areas of the holes (31) as measured in the cross section of the holes in or on the surface (32) of the sublayer (30) that faces the wearer). Preferably the open area of a region (33) with holes (31) of the sublayer (30) is from 25% to 45% or even more preferably from 30% to 40% or to 35% of the total surface area of the region.

The sublayer (30) may comprise one or more regions with holes (31), typically such that the region(s) is (are) at least present in the crotch and/or back region of the sublayer (30), as shown in FIGS. 8 and 9. In one preferred execution, shown in FIGS. 8 and 9, the sublayer (30) comprises a single region (33) with combined holes (31), typically in the back region (44) and part of the crotch region (43) of the article, e.g. the back ⅔ or 65% or less of the surface area of the topsheet or diaper (10), preferably the back 60% or even more preferably the back 50% thereof.

Preferred is that the open area of the sublayer as a whole is less than 45%, preferably between 15% and 40%, or more preferably between 20% and 35%.

The first (36) and second (37) and further acquisition layers of the sublayer (30) may all have the same width and length dimensions, but it may be preferred that the first acquisition layer (36) ahs a larger width and/or length then the second layer.

Furthermore, the absorbent article (10) herein has typically a topsheet (20); then, the sublayer (30) may have the same width and/or length as the topsheet (20), but preferably the sublayer (30) has a smaller width dimension and/or optionally a smaller length dimension than the topsheet (20). FIG. 1 shows such an execution whereby the width of the sublayer (30) is smaller than the width of the topsheet (20). FIG. 10 shows an embodiment whereby the length of the sublayer (30) is smaller than the length of the topsheet (20).

Preferably, the surface of the sublayer (30) that faces the wearer (and topsheet (20)) and the surface of the sublayer that faces the backsheet (12) (and absorbent core 11) are flat.

When the combined holes (31) in the sublayer (30) are blind holes (38), as shown in FIGS. 6 and 7, then the combined holes (31) typically have an average caliper or depth that is at least 70%, or preferably at least 80%, or when possible even at least 95% of the average caliper of the sublayer (30) or relevant region (33) thereof.

The sublayer (30) (and the combined through holes (31) of the sublayer (30)) have preferably an average caliper or depth (34, 35) of at least 2 mm, preferably at least 3 mm, or even at least 4 mm, at least in the regions (33) of the sublayer (30) that comprises said holes. The preferred maximum caliper of the sublayer may be 8 mm or more preferably 6 mm, for wearer's comfort.

The caliper or depth (35) of the holes is determined by the method set out herein below.

The sublayer (30) is preferably compression resistant even after wetting, such that is its average caliper (34) loss (wet resilience) is less than 20% or even more preferably less than 15%, or even more preferably less than 12%, or preferably even less than 10% compared to the average caliper (34) of the dry sublayer (30) before wetting, under the same pressure. This is determined by the method set out herein below.

Preferred articles (10) herein have at least three layers with apertures (21) or holes (31), namely a topsheet (20) with apertures (21) and a sublayer (30) comprising at least said two acquisition layers with holes that form the combined holes (31) of the sublayer. Preferred topsheets (20) are described below. Preferred is that the regions with apertures (21) of the topsheet (20) and the regions with combined holes (31) of the sublayer (30) have a certain overlap, as described herein below.

A preferred second acquisition layer (37) comprises unbonded polypropylene (PP) and/or polyester fibres, or preferably polyethylene teraphthalate (PET) fibres.

Alternatively, or in addition, it may be highly preferred that the second acquisition layer (37) comprising a modified (cellulose) fibers, preferably chemically stiffened, twisted and/or curled (curly) (cellulose) fibres, preferably chemically stiffened, twisted and/or curled crosslinked cellulose or crosslinked synthetic fibres, preferably cellulose fibres. Preferred may be materials available from Weyerhaeuser under as CMC520 and CMC517.

Preferred first acquisition layers (36) include nonwoven acquisition layers, including carded bonded nonwoven acquisition layers, such carded resin-bonded nonwovens, embossed carded resin-bonded nonwoven acquisition layers, and optionally highloft carded resin-bonded nonwoven acquisition layers, or preferably carded through-air-bonded nonwoven acquisition layers, carded thermo-bonded nonwoven acquisition layers; most preferably are non-embossed carded resin-bonded non-woven acquisition layers. Preferred are such materials with a high basis weight, i.e. of 40 gsm or more, preferably even 60 gsm Materials as above that may be used herein as first acquisition layer (36) are available from BBA Fiberweb/Tenotex (Italy) under the trade name Printex AQL1 Phil (43 gsm, white); or from Freudenberg/Halifax under the code AL 1060 (SC V and SO, and AR10) and under the code 114/011/05 (typically 43 or 60 gsm); or from Lohmann, under the trade name Paraprint.

The sublayer (30) may be made by forming holes (31) in a continuous sublayer (30) (i.e. without holes (31)), for example by punching or pushing holes (31) in a said sublayer (30), either in two or more acquisition layers (36, 37) at the same time, or separately and subsequently placing the layers such that the holes in the first and second layer are aligned with one another, to form the combined holes (31).

When the sublayer (30) comprises two or more layers, it may be beneficial that the holes (31) are formed by pushing, e.g. by pushing a hole forming tool onto the surface of the first layer (36) and through the first and second layer (37) and further layers, such that part of the material of the first layer (36) is pushed into the holes in the second and optionally further layers, to cover (part of) the side-walls of the holes (31). As described above, this may provide smooth edges and walls of the holes (31), and furthermore it may inhibit the fibres of the second layer (37) to migrate into the holes (31), and come into contact with the skin of the user. This embodiment whereby the first layer (36) is present on the walls of the holes (31) is shown in FIG. 5.

It may also be preferred to form the holes (31) of the sublayer (30) by laying down the material, e.g. fibres, of the second and optionally further layers (37) on a forming surface, around for example protrusions or around shaped portions that hereby shape the holes (31). For example, fibres may be laid down on a forming drum with protrusions in the required hole-pattern of the sublayer (30), around said protrusions to thus shape the holes (31), and the fibres may then optionally be (partially) bonded by known bonding techniques. Then, the first acquisition layer (36) may be placed onto the second layer (37) and optionally bonded thereto. This first acquisition layer (36) may already comprise holes that are then aligned with the holes of the second acquisition layer (37), or the holes may still be made in the first acquisition layer after placing this on the second layer, or the first layer may be pushed into the second layer (37) to form indentations in the first layer 936), into the holes of the second layer (37).

It may also be preferred that a second (37) and optional further layers with holes are first obtained and subsequently a first layer (36) is placed onto the second layer, or optionally further layers, and the first layer is then partially pushed into the holes of the second (37) and further layers, to form the sublayer (30) described above.

It may also be preferred that the sublayer (30) comprises one or more layers formed by one of the methods above and one or more layers formed by a different method, as described above. For example, a sublayer (30) may comprise a second layer (37) formed by the lay-down technique above and a first layer (36) formed by punching or pushing, whereby the second holes (31) are punched or pushed either prior to combining the two or more layers, or after combining the two or more layers.

In another embodiment, there may be a caliper (34) gradient of the combined holes (31) in a region of the sublayer (30), or between different regions (31) of the sublayer (30), so that for example the holes (31) in one (part of a) region (31) have a greater caliper than in another region (31) or than in another part of the same region (31).

Topsheet (20)

The articles (10) of the invention comprises preferably a topsheet, present on the sublayer, that in use is in contact with the skin of the user, and said topsheet 920) preferably comprises apertures (21) that are through-apertures (21), i.e. where the apertures (21) are through the whole thickness (z-direction) of the topsheet (20).

This allows feces to migrate through the topsheet (20) to the sublayer (30).

The topsheet (20) may be embossed, but in a preferred embodiment, the topsheet (20) is flat and the average caliper of the topsheet (20) equals the average caliper or depth of the apertures (21), as shown in FIG. 2.

The apertures (21) of the topsheet (20) are small, having an average greatest dimension (in the plane of the topsheet (20)) of from 2 to 8 mm, preferably from about 2 mm to 6 mm, or even more preferably from 2.4 to 6 mm, or even more preferably from 3 to 5 mm or to 4 mm.

Preferably, the apertures (21) have also an average smallest dimension of from 2 mm to 6 mm, and preferably from 3 to 5 mm.

The average aperture dimension when used herein is determined in the cross section of the apertures that is on the surface of the topsheet (20) that faces in use the body of the wearer, by the method said out below.

Preferably, the apertures (21) are such that the greatest dimension is through the centre point of the aperture (21). Preferably, the apertures (21) have an oval and/or circular circumference, as shown in FIGS. 1 and 2.

The average shortest (smallest) distance between the middle points of neighboring apertures (21) is preferably from 2 to 7 mm, or more preferred from 4 to 6 mm.

Each region (23) of apertures (21) has an open area, which is the sum of the surface areas of said apertures (21) of said region (23), as measured in the cross section of the apertures (21) in the body facing surface of the topsheet (20). This can be determined by the method described herein below.

This open area of each region (23) is preferably from 20% to 55% of the total surface area of said region, and preferably from 30% to 50%, or even more preferably from 30% to 45% thereof.

Preferably, at the total open area of the topsheet (20) (which is the sum of open area of the regions with apertures (21) of the topsheet (20)) is from 15% to 55%, and preferably from 20% to 50% or even more preferably from 25% or 30% to 45%, of the total surface area of the topsheet (20).

Preferably the topsheet (20) comprises a single region (23) with apertures (21) which is typically about 60% to 100% of the total surface area of the topsheet (20), preferably about 80% to 100% of the total surface area of the topsheet (20). Thus, in a preferred execution, the whole topsheet (20) comprises said apertures (21) and thus, there is only one region with apertures (21) in the topsheet (20) that is 100% of the topsheet (20) surface area, as is shown in FIGS. 1 and 2.

Another preferred execution, the topsheet (20) has one region (23) with apertures (21) that is centered in the topsheet (20), such that said region is not present along the longitudinal and transverse edges of the topsheet (20), i.e. so that no apertures (21) are present along said edges.

The topsheet (20) can be made of liquid permeable or impermeable material, because due to the apertures (21), the urine and feces will pass easily and quickly to the sublayer (30) and the absorbent core below. The topsheet (20) may be (made of) a nonwoven or woven web with apertures (21) that is made of synthetic and/or natural fibers, or it may be an apertured or apertured formed polymer film, or a combination thereof, as known in the art and for example described in U.S. Pat. No. 5,342,338 and EP-A-0203823.

Preferred apertured topsheets include fibrous nonwoven webs, made of polyolefin, preferably of polyethylene, polypropylene or copolymers thereof, or mixtures thereof.

Preferred topsheets (20) herein are made by forming apertures (21) in a continuous uninterrupted film or web of a thermoplastic polymer, for example polyolefins, and/or by providing a film or web with a plurality of spaced apart discrete bonds and weakening the web or film at a plurality of locations whereby a portion of the spaced part nods are separated from said weakened locations, and subsequently applying a tensioning force to said web or film to rupture the weakened locations, e.g. by stretching said film or web, to form thus apertures.

Preferred processes for making apertured films or webs as used herein are described in U.S. Pat. No. 5,916,661, U.S. Pat. No. 5,658,639 and U.S. Pat. No. 5,628,097.

The nonwoven webs with apertures (21) useful herein as topsheet (20) comprise preferably polyethylene and/or polypropylene and/or polyester fibers and preferably have a basis weight of about 15 to 30 $g/m^2$ or to 25 $g/m^2$. Preferred are carded nonwoven webs, including carded hydro-entangled and carded through-air bonded nonwoven webs. The topsheet (20) is typically non-liquid retaining in use, to ensure the liquid (e.g. urine) is transported immediately through the topsheet (20) (the apertures (21) thereof and optionally through the topsheet (20) material itself) to the underlying acquisition sublayer (30) and absorbent core (11).

The topsheet (20) may comprise a skin care lotion as known in the art. It may be preferred that this is applied in the form of stripes on the topsheet (20), preferably in the form of longitudinal (Machine Direction) stripes.

The topsheet (20) may be completely or partially attached to the sublayer (30) described herein after. This may be done by any known method in the art, preferred methods include adhesive bonding. It may be preferred that the topsheet (20) and sublayer (30) are only partially attached to one another, for example 50% to 80% of the corresponding surface area between the topsheet and sublayer.

Unlike the sublayer (30) described above, the topsheet (20) is thin, e.g. less than 1.0 mm or typically even less than 0.5 mm thick, and may be hydrophilic or hydrophobic, because it merely serves to pass the liquid and feces directly through to the sublayer (30) below, and will typically not contain the liquid or distribute the liquid in x and y direction.

The topsheet (20) overlies the sublayer (30) either partially, or typically completely, as shown in FIGS. 1, 2 and 12. This includes the embodiment that the sublayer (30) has a smaller surface area than the topsheet (20), either having a smaller width (cross-machine direction) or length (machine direction) or both, as shown in FIGS. 1, 2 and 12.

Typically, at least one region (23) with apertures (21) of the topsheet (20) overlies a region with holes (31) of the sublayer (30), either partially or completely, such that an overlap-zone (40) exists, where at least some of the apertures (21) are positioned above at least some of the holes (31), completely and/or partially, to form combined apertures. (42).

The combined apertures (42) allow direct passage of feces (and liquids) from the user through the topsheet (20) into the holes (31) of the sublayer (30).

However, the region(s) (33) of the sublayer (30) and the holes (31) thereof, and the region (23) of the topsheet (20) and the apertures (21) thereof, and the overlap-zone (40) are created such that the amount of feces that can transfer back to the skin of the user is minimised, whilst still allowing the required passage of the feces to the holes (31) of the sublayer (30) and immobilisation and isolation of the feces in the holes (31) of the sublayer (30).

The overlap-zone (40) has thereto preferably an open area (which is the sum of the surface areas of the combined apertures (42) therein in the plane of the body facing surface of the topsheet (20)) of from 15% to 50% of the surface area of said overlap-zone, or preferably 20% to 45% or even more preferably 25% to 35%.

Typically, the total surface area of said overlap-zone (40) is at least 2 cm×3 cm (CD×MD) in order to have sufficient surface area to receive the feces and transport it through the apertures (21) into the holes (31). Hereby the width and length dimensions of 2×3 cm are average values. (More than one overlap zone (40) may be present and than the total of the overlap zones (40) should be at least 2 cm×3 cm as above, but preferably each overlap zone (40) is at least 2 cm×3 cm as above.)

Preferred is that the overlap zone (40) is present in the back and crotch portions of the article (diaper), or part thereof, but not in the front portion of the article (diaper).

In a preferred embodiment, the absorbent article (10) has one single overlap zone (40), and preferably also only one region (33) of holes (31) in the sublayer (30), and the topsheet (20) overlays this region completely, and then this single overlap zone (40) is preferably at least positioned in the crotch (43) and/or back portion (44) of the article, as described above, as shown in FIG. 12, e.g. in the back 70% of the surface area of the article (10) or topsheet (20) thereof.

The overlap zone (40) may have any shape, including circular, oval, rectangular, triangular, or square. Since the region (33) of the sublayer (30) is typically smaller in surface area than the region (23) of the topsheet (20), the shape of the overlap area is typically determined by the shape of the sublayer (30), as shown in FIGS. 8, 9 and 10.

The sublayer (30) (and/or the topsheet (20)) may comprise registrable marks that allow registration of the sublayer (30) and its holes (31) thereof (and/or the topsheet (20) and its apertures (21)) to allow correct alignment and/or partial alignment of the holes (31) of the sublayer (30) and the apertures (21) of the topsheet (20).

Test Methods Referred Herein
Open Area Determination; Aperture and Hole Dimensions and Surface Areas Determination The open area of the regions (23, 33) of the sublayer (30), topsheet (20) and of the overlap-zone (40) as used herein can be determined by light microscopy as follows.

Depending on the size of the region (23, 33) or overlap zone (40), said region or overlap zone (40) is each analyzed either as a whole, or in separate portions, to reach an open area value of the whole region (23, 33) or overlap zone (40).

To determine the open area of the overlap zone (40), a sample is prepared by taking the topsheet (20) and the sublayer (30) to be analyzed from the absorbent article, in such a manner that they do not move with respect to one another, in order to keep the overlap-zone (40) the same. Alternatively, the sublayer (30) and topsheet (20) are first marked such that after removal from the article, the topsheet (20) can be placed onto the sublayer (30) in its original position, to obtain the same overlap zone (40).

Then, the open area and aperture dimensions of the overlap zone (40) can be determined (by measuring and viewing the surface area that in use faces the user).

To determine the open area and aperture/hole dimensions of the topsheet (20) and sublayer (30), these will have to be separated in the above sample, or new samples of the topsheet (20) and sublayer (30) will have to be made for analyses.

Any sample size can be submitted to the light microscopy, but typically the sample will not be bigger than 15×15 cm. If the region and/or sublayer (30) is or are bigger than this, they may be cut into separate samples by any suitable technique, and each sample can be measured.

The light microscope (JAI CV-M1 E Monochromic Camera; with as lens a Micro-zoom-0.1-0.7) is connected to an interface (ITI-Vision-Itex) that is connected to a computer that runs Optimas software (Media Cybernetics, L.P. Optimas version 6.51) that will do all calculations. Any suitable external light source may be used, for example Kaiser e-Vision.

The sample is placed onto a black cardboard without stretching, without wrinkles or folds. This is placed under the light microscope and the zoom is adjusted to 3.5 and focused until a clear picture is obtained. Then the sample is removed and a ruler is placed under the microscope.

The calibration is then started with the software.

The software will calculate the average smallest and greatest aperture or hole sizes in the cross sections of the apertures and holes on the surface, and the total or average open areas thereof.

The measurement can be repeated twice to obtain 3 values and an average thereof, which is referred herein throughout the specification.

Caliper (34)

The caliper of (the topsheet (20) and) the sublayer (30), or the part thereof that is present in the overlap zone, and of the apertures (21) or holes (31) thereof are determined by use of a (calibrated) Micrometer, under 23° C. and 50% humidity conditions, whereby the Mircometer as an accuracy minimum of 0.01 mm, lowering speed of 3 mm/s, dwelling time of 2-5 sec., such as for example a Frank Type 16303 available from Twing Albert-Frank Gmbh. The Micrometer has a loading 266 grams and an anvil 40 mm in diameter (resulting in 0.3 psi).

The material to be measured is equilibrated for at least 2 hours at 23° C. and 50% humidity prior to the measurement. If the material is to be cut prior to the measurement, the cutting should be done such that the caliper does not change, e.g. without compression in the area that is to be measured. The material should be free of wrinkles, folds, or defects in the area that is to be measured.

The material is placed under the micrometer and the caliper is recorded after the dwelling time.

Five samples can be made and measured to calculate the average over five samples, which is referred to herein.

Caliper (34) Loss after Wetting (Wet Resilience)

The following test method determines the wet resilience of the sublayer (30) (that is part of the overlap zone (40)) under a pressure of 0.3 psi, after wetting the sublayer (30), and this is translated in the caliper loss values referred herein.

The sublayer (30) and topsheet (20) are removed from the absorbent article (10). (For measurement purposes, the topsheet (20) is included in this measurement, but the caliper values of the topsheet (20) are deducted, as described below).

In some embodiments, the sublayer (30) may be enclosed between an absorbent core cover (13) and the topsheet (20), in particular when the sublayer (30) is not a web or film, but comprises for example only partially bonded or non-bonded fibers. If such a core cover or core wrap (13) is present, this should be removed from the article together with the sublayer (30) and the topsheet (20), to obtain the sample used herein, containing the core cover (13), sublayer (30) and topsheet (20).

The samples are conditioned for 2 hours at 23° C., 50% humidity and the tests are conducted at the same conditions.

Then, the weight of each sample is determined by any standard method.

First, under a pressure of 0.3 psi, the caliper (34) of the dry sample as a whole and the caliper of the topsheet (20) and optionally the core cover are determined. The caliper (34) under said pressure of the topsheet (20) and optionally the core wrap (13) are deducted from the overall caliper, to obtain the caliper (34) under pressure of the dry sublayer (30). The caliper of the sublayer (30) and topsheet (20), and optionally the core cover (13), are measured in the overlap zone (40), by measuring the caliper thereof in at least 3 points and taking the average thereof (hereinafter referred to as the (average) dry caliper (34) under pressure). The same is done for the caliper under pressure of the topsheet (20) and optionally the core cover (13) (which may be combined into one set of measurements to obtain their combined average caliper under pressure).

Then the dry calipers are measured as set out above, with a Micrometer (e.g. Frank type 16303) with a pressure foot diameter of 40 mm, with a pressure of 0.3 psi, with a lowering speed of 3 mm/s.

Caliper readings are taken 1 minute after the pressure foot is contacted with the surface of the sample.

Then, the sample is loaded with 10 ml saline solution (0.9% NaCl in de-mineralized water) per gram sample, by gently pouring the saline solution along the y-direction centre line of the sample, by slowly moving up and own along said centre line and pouring the saline with a speed of approximately 1 ml/sec. Then the caliper of the sample and the topsheet (20) and optionally core wrap at exactly the same points as before, but after wetting is determined as described above.

The average dry and wet calipers of the sublayer, as referred to herein are calculated as follows:

Average Dry Caliper of the Sublayer =
  (average dry calpier of the sample comprising sublayer, topsheet, and optionally the core wrap) −
  (average dry caliper of the topsheet plus optionally core wrap).

Average Wet Calpier of the Sublayer =
  (average wet calpier of the sample comprising sublayer, topsheet, and optionally the core wrap) −
  (average wet caliper of the topsheet plus optionally core wrap).

The percentage calpier (34) loss is then calculated as follows:

$$\frac{(Av.\ Dry\ Caliper\ of\ the\ Sublayer) - (Av.\ Wet\ Caliper\ of\ the\ Sublayer)}{(Av.\ Dry\ Caliper\ of\ the\ Sublayer)} \times 100\%$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for receiving and storing bodily exudates, the absorbent article comprising:
   a. a backsheet and a topsheet; and
   b. a sublayer positioned between the topsheet and backsheet comprising a wearer faceable surface, an opposing garment faceable surface, a first acquisition layer and a second acquisition layer, said second acquisition layer being positioned between the backsheet and the first acquisition layer, said sublayer comprising one or more areas with a plurality of combined holes, being formed by at least one of (i) holes extending through said first acquisition layer and holes in or extending through said second acquisition layer, or (ii) by holes in or extending through said second acquisition layer and indentations in said first acquisition layer, wherein said article, sublayer, holes, and combined holes each have a length in the y-direction, width in the x-direction and caliper in the z-direction, said second acquisition layer comprising non-bonded fibers, said combined holes having an average smallest dimension in an x-y cross section of the combined holes in the wearer faceable surface of said sublayer of at least 2 mm, surface areas of the x-y cross section of the holes through or indentations in the first acquisition layer as measured on the wearer faceable surface are less than corresponding surface areas of the x-y cross section of the holes in or through the second acquisition layer as measured on a surface of the second layer that faces the first layer, and wherein, in the z-direction, the x and y dimensions of the first acquisition layer holes or indentations align with the x and y dimensions of the second acquisition layer holes.

2. The absorbent article of claim 1, whereby the first acquisition layer comprises holes and all x-y cross sections of the holes through the first layer have surface areas that are smaller than the surface areas of all x-y cross sections of the holes in or through the second layer.

3. The absorbent article of claim 1, whereby said average smallest dimension of the combined openings is from 4 mm to 8 mm and said sublayer has an open area of from 20% to 50% of a total surface area of said sublayer, as measured on the wearer faceable surface.

4. The absorbent article of claim 1, whereby said second layer comprises a non-bonded or partially bonded fibrous material selected from: chemically stiffened curled fibrous material, synthetic polyester fibers, or a mixture thereof, or a mixture of pulp and synthetic polyester fibers, or a mixture of pulp and chemically stiffened curled fibrous material.

5. The absorbent article of claim 1, whereby said sublayer has an average caliper of from 3 mm to 6 mm.

6. The absorbent article of claim 1, wherein said sublayer has an average caliper loss after wetting and under a pressure of 0.3 psi of less than 20%.

7. The absorbent article of claim 1, whereby said average smallest dimension of the combined openings is from 4 mm to 8 mm and said sublayer has an open area of from 20% to 50% of said area of combined holes, as measured on the wearer faceable surface.

* * * * *